United States Patent
Campbell et al.

(10) Patent No.: US 9,975,901 B2
(45) Date of Patent: May 22, 2018

(54) CRYSTALLINE SOLID STATE FORM OF THE BENZENE SULPHONIC ACID SALT OF 2-[(4S)-6-(4-CHLOROPHENYL)-1-METHYL-8-(METHYLOXY)-4H-[1,2,4]TRIAZOLO[4,3-A][1,4]BENZODIAZEPIN-4-YL]-N-ETHYLACETAMIDE

(71) Applicant: GlaxoSmithKline Intellectual Property (No.2) Limited, Brentford, Middlesex (GB)

(72) Inventors: Gossett Augustus Campbell, Collegeville, PA (US); Asa Elisabeth Gladwin, Stevenage (GB)

(73) Assignee: GlaxoSmithKline Intellectual Property (No. 2) Limited, Brentford, Middlesex (GB)

( * ) Notice: Subject to any disclaimer, the term of this patent is extended or adjusted under 35 U.S.C. 154(b) by 0 days. days.

(21) Appl. No.: 15/515,683

(22) PCT Filed: Sep. 30, 2015

(86) PCT No.: PCT/EP2015/072515
§ 371 (c)(1),
(2) Date: Mar. 30, 2017

(87) PCT Pub. No.: WO2016/050821
PCT Pub. Date: Apr. 7, 2016

(65) Prior Publication Data
US 2017/0298071 A1     Oct. 19, 2017

Related U.S. Application Data

(60) Provisional application No. 62/058,753, filed on Oct. 2, 2014.

(51) Int. Cl.
| | | |
|---|---|---|
| A61K 31/551 | (2006.01) | |
| C07D 487/04 | (2006.01) | |
| C07C 309/29 | (2006.01) | |
| A61K 31/5517 | (2006.01) | |
| A61K 9/00 | (2006.01) | |
| A61K 9/20 | (2006.01) | |

(52) U.S. Cl.
CPC .......... *C07D 487/04* (2013.01); *A61K 9/0053* (2013.01); *A61K 9/2027* (2013.01); *A61K 31/5517* (2013.01); *C07C 309/29* (2013.01); *C07B 2200/13* (2013.01)

(58) Field of Classification Search
CPC ............................ A61K 31/551; C07D 487/04
USPC .......................................... 514/220; 540/566
See application file for complete search history.

(56) References Cited

FOREIGN PATENT DOCUMENTS

| WO | 2011054553 A1 | 5/2011 |
|---|---|---|
| WO | 2011054845 A1 | 5/2011 |

OTHER PUBLICATIONS

Caira, Crystalline Polymorphism of Organic Compounds. Design of Organic Solids. Topics in Current Chemistry, Springer Verlag Berlin Heidelberg; 1998. 198:163-208.

*Primary Examiner* — Brenda L Coleman
(74) *Attorney, Agent, or Firm* — Duke M. Fitch; Kathryn A. Lutomski; Edward R. Gimmi

(57) ABSTRACT

The present invention relates to a salt form of a benzodiazepine derivative, in particular crystalline solid state forms, to pharmaceutical compositions comprising the same and to its use in therapy.

11 Claims, 2 Drawing Sheets

CRYSTALLINE SOLID STATE FORM OF THE BENZENE SULPHONIC ACID SALT OF 2-[(4S)-6-(4-CHLOROPHENYL)-1-METHYL-8-(METHYLOXY)-4H-[1,2,4]TRIAZOLO[4,3-A][1,4]BENZODIAZEPIN-4-YL]-N-ETHYLACETAMIDE

This application is a § 371 of International Application No. PCT/EP2015/072515, filed 30 Sep. 2015, which claims the benefit of U.S. Provisional Application No. 62/058,753, filed 2 Oct. 2014, which are incorporated herein in their entireties.

FIELD OF THE INVENTION

The present invention relates to a benzene sulphonic acid (besylate) salt of a benzodiazepine derivative, to pharmaceutical compositions comprising the same and its use as a therapeutic agent for treating a number of diseases or conditions. In particular, the present invention relates to a crystalline solid state form of a benzene sulphonic acid salt, to processes for its preparation and its use in the treatment of diseases or conditions for which a bromodomain inhibitor is indicated.

BACKGROUND OF THE INVENTION

Patent applications WO2011/054553 and WO2011/054845 (both in the name of GlaxoSmithKline LLC) disclose the compound 2-[(4S)-6-(4-chlorophenyl)-1-methyl-8-(methyloxy)-4H-[1,2,4]triazolo[4,3-a][1,4]benzodiazepin-4-yl]-N-ethylacetamide as a BET family bromodomain inhibitor and describes therapeutic uses thereof. The chemical structure of this compound is represented by formula (I):

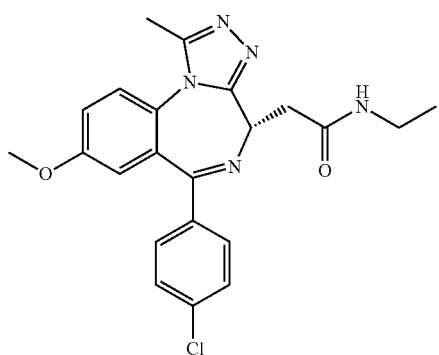

(I)

There remains the need to identify a form of the compound of formula (I), which provides suitable properties for its development as a pharmaceutical product. In particular, a form of the compound of formula (I) which provides one or more suitable properties such as hydroscopicity, stability, solubility and processability is required.

SUMMARY OF THE INVENTION

In a first aspect of the present invention, there is provided a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide, in particular crystalline forms thereof.

In a second aspect of the present invention, there is provided processes for the preparation of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide, including crystalline forms thereof, and to intermediates used in such processes.

In a third aspect of the present invention, there is provided a pharmaceutical composition comprising a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide and one or more pharmaceutically acceptable excipient(s).

In a fourth aspect of the present invention, there is provided a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide for use in therepy, particularly for use in treating diseases or conditions for which a bromodomain inhibitor is indicated.

In a fifth aspect of the present invention, there is provided a method of treating diseases or conditions for which a bromodomain inhibitor is indicated in a subject in need thereof which comprises administering a therapeutically effective amount of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide.

In a sixth aspect of the present invention, there is provided the use of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in the manufacture of a medicament for the treatment of diseases or conditions for which a bromodomain inhibitor is indicated.

DETAILED DESCRIPTION OF THE INVENTION

The present invention provides in a first aspect a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide. It will be appreciated that a benzene sulphonic acid salt could also be referred to as a besylate salt or as a benzene sulphonate salt.

In one embodiment the present invention provides a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide, that is to say the compound of formula (II)

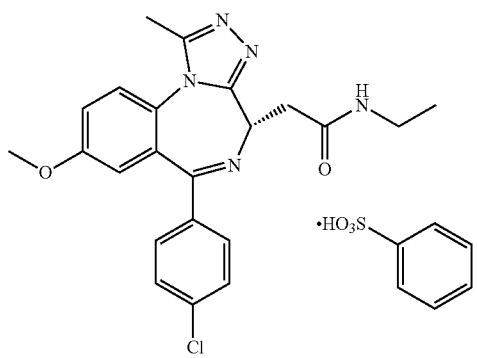

The compound of formula (II) typically contains between about 0.90 and about 1.10 molar equivalents of benzene sulphonic acid per molar equivalent of 2-[(4S)-6-(4-chlorophenyl)-1-methyl-8-(methyloxy)-4H-[1,2,4]triazolo[4,3-a][1,4]benzodiazepin-4-yl]-N-ethylacetamide; including between about 0.95 and about 1.05 molar equivalents of benzene sulphonic acid. In a particular embodiment, the salt of this invention contains about 1 molar equivalent benzene sulphonic acid per molar equivalent of 2-[(4S)-6-(4-chlorophenyl)-1-methyl-8-(methyloxy)-4H-[1,2,4]triazolo[4,3-a][1,4]benzodiazepin-4-yl]-N-ethylacetamide. Such molar ratio can be readily determined by various methods available to those skilled in the art, for example, by $^1$H NMR or by elemental analysis.

It will be appreciated that a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide could be in any suitable anhydrous, solvated (e.g. hydrated) and/or polymorphic forms thereof.

The present invention further provides a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in a crystalline solid state form.

In one embodiment there is provided a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in a crystalline anhydrous solid state form.

Figure 1:
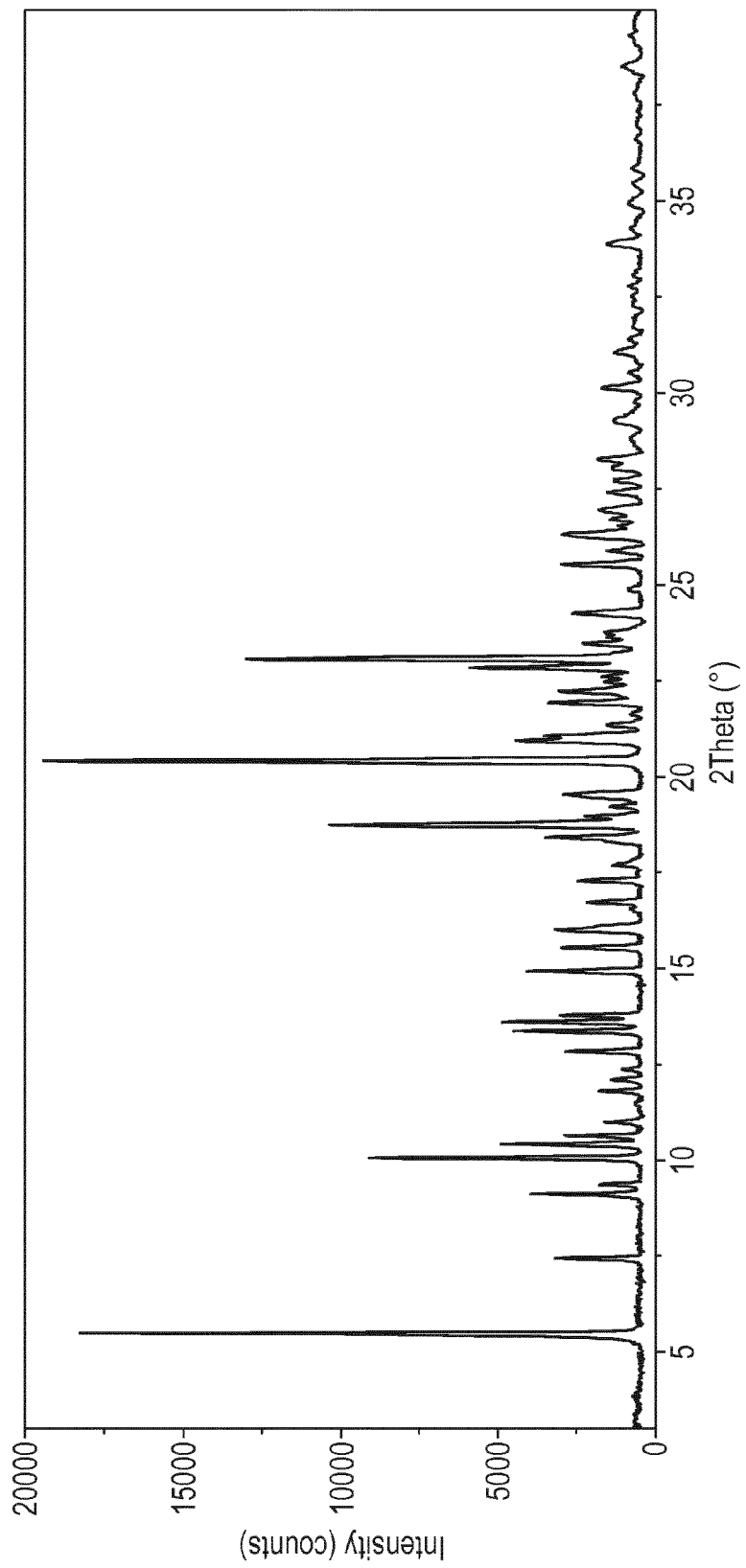
FIG. 1: Showing the X-ray powder diffraction (XRPD) pattern recorded for a crystalline solid state form of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide.

In one embodiment the invention provides for a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in crystalline solid state form characterised by an X-ray powder diffraction (XRPD) pattern substantially as shown in FIG. 1, wherein the XRPD pattern is expressed in terms of degrees 2 theta angles and obtained with a diffractometer using copper Kα-radiation using procedures described herein.

In one embodiment the invention provides for a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in crystalline solid state form characterised by an X-ray powder diffraction pattern comprising at least three diffraction angles, expressed in degrees 2θ, selected from a group consisting of about 5.5, 7.4, 9.1, 10.0, 10.4, 13.3, 13.6, 14.9, 18.7, 20.4, 20.9, 22.8 and 23.1° (±0.1°).

In another embodiment the invention provides for a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in crystalline solid state form characterised by an X-ray powder diffraction pattern comprising at least ten diffraction angles or at least nine diffraction angles or at least eight diffraction angles or at least seven diffraction angles or at least six diffraction angles or at least five diffraction angles or at least four diffraction angles, expressed in degrees 2θ, selected from a group consisting of about 5.5, 7.4, 9.1, 10.0, 10.4, 13.3, 13.6, 14.9, 18.7, 20.4, 20.9, 22.8 and 23.1° (±0.1°).

In another embodiment the invention provides for a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in crystalline solid state form characterised by an X-ray powder diffraction pattern comprising diffraction angles, expressed in degrees 2θ, at about 5.5, 10.0, 18.7, 20.4, and 23.1° (±0.1°).

An XRPD pattern will be understood to comprise a diffraction angle (expressed in degrees 2θ) of "about" a value specified herein when the XRPD pattern comprises a diffraction angle within ±0.1 degrees 2θ of the specified value. Further, it is well known and understood to those skilled in the art that the apparatus employed, humidity, temperature, orientation of the powder crystals, and other parameters involved in obtaining an X-ray powder diffraction (XRPD) pattern may cause some variability in the appearance, intensities, and positions of the lines in the diffraction pattern. An X-ray powder diffraction pattern that is "substantially as shown in FIG. 1" provided herein is an XRPD pattern that would be considered by one skilled in the art to represent a compound possessing the same crystal form as the compound that provided the XRPD pattern of FIG. 1. That is, the XRPD pattern may be identical to that of FIG. 1, or more likely it may be somewhat different. Such an XRPD pattern may not necessarily show each of the lines of any one of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. For example, one skilled in the art can overlay an XRPD pattern of a sample of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide, with FIG. 1 and, using expertise and knowledge in the art, readily determine whether the XRPD pattern of the sample is substantially as shown in FIG. 1.

Figure 2:
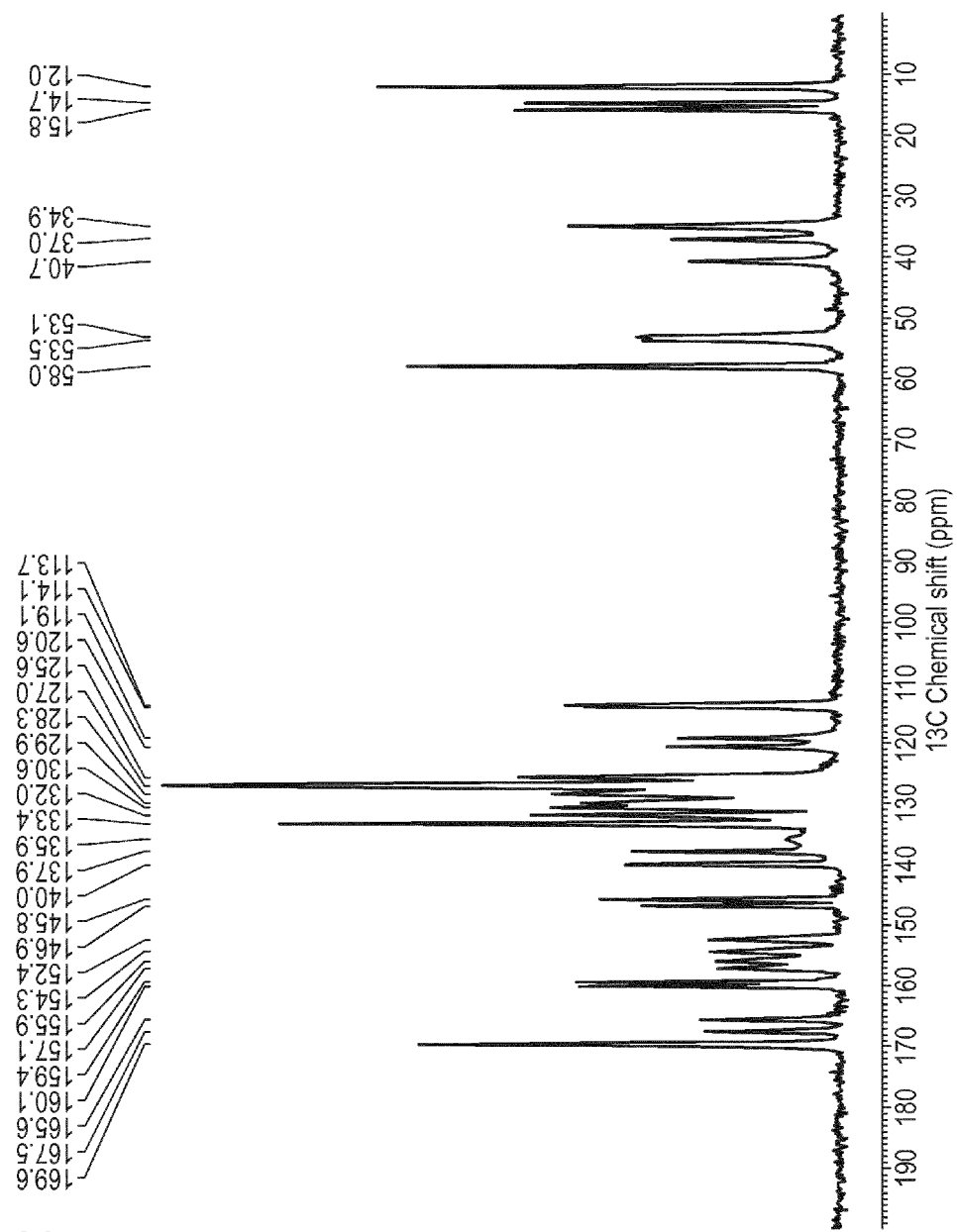
FIG. 2: Showing the $^{13}$C solid state NMR (SSNMR) spectrum recorded for a crystalline solid state form of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide.

In one embodiment the invention provides for a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in crystalline solid state form characterised by a $^{13}$C SSNMR spectrum substantially as shown in FIG. 2.

In one embodiment the invention provides for a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in crystalline solid state characterised by a $^{13}$C SSNMR spectrum comprising at least ten peaks, expressed as chemical shifts in ppm, selected from a group consisting of peaks at about 169.6, 167.5, 165.6, 160.1, 159.4, 157.1, 155.9, 154.3, 152.4, 146.9, 145.8, 140.0, 137.9, 135.9, 133.4, 132.0, 130.6, 129.9, 128.3, 127.1, 125.6, 123.5, 120.6, 119.1, 114.1, 113.7, 58.0, 53.6, 53.1, 40.7, 37.0, 34.9, 15.8, 14.7, and 12.0 (±0.2 ppm).

In one embodiment the invention provides for a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in crystalline solid state characterised by a $^{13}$C SSNMR spectrum comprising at least twenty peaks or at least eighteen peaks or at least sixteen peaks or at least fourteen peaks or at least twelve peaks, expressed as chemical shifts in ppm, selected from a group consisting of peaks at about 169.6, 167.5, 165.6, 160.1, 159.4, 157.1, 155.9, 154.3, 152.4, 146.9, 145.8, 140.0, 137.9, 135.9, 133.4, 132.0, 130.6, 129.9, 128.3, 127.1, 125.6, 123.5, 120.6, 119.1, 114.1, 113.7, 58.0, 53.6, 53.1, 40.7, 37.0, 34.9, 15.8, 14.7, and 12.0 (±0.2 ppm).

A $^{13}$C SSNMR spectrum will be understood to comprise a peak (expressed in ppm) of "about" a value specified herein when the $^{13}$C SSNMR spectrum comprises a peak within ±0.2 ppm of the specified value. Further, it is also well known and understood to those skilled in the art that the apparatus employed, humidity, temperature, orientation of the powder crystals, and other parameters involved in obtaining a $^{13}$C SSNMR spectrum may cause some variability in the appearance, intensities, and positions of the peaks in the spectrum. A $^{13}$C SSNMR spectrum that is "substantially as shown in FIG. 2" provided herein is a $^{13}$C SSNMR spectrum that would be considered by one skilled in the art to represent a compound possessing the same crystal form as the compound that provided the $^{13}$C SSNMR spectrum of FIG. 2. That is, the $^{13}$C SSNMR spectrum may be identical to that of FIG. 2, or more likely it may be somewhat different. Such a $^{13}$C SSNMR spectrum may not necessarily show each of the peaks of any one of the spectra presented herein, and/or may show a slight change in appearance, intensity, or a shift in position of said peaks resulting from differences in the conditions involved in obtaining the data. A person skilled in the art is capable of determining if a sample of a crystalline compound has the same form as, or a different form from, a form disclosed herein by comparison of their $^{13}$C SSNMR spectra. For example, one skilled in the art can overlay a $^{13}$C SSNMR spectrum of a sample of a benzene sulphonic acid salt of 2-[(4S)-6-(4-chlorophenyl)-1-methyl-8-(methyloxy)-4H-[1, 2,4]triazolo[4,3-a][1,4]benzodiazepin-4-yl]-N-ethylacetamide, with FIG. 2 and, using expertise and knowledge in the art, readily determine whether the $^{13}$C SSNMR spectrum of the sample is substantially as shown in FIG. 2.

In still further embodiments, as a person having ordinary skill in the art will understand, a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide may be characterized by a combination of the analytical data characterising each and all of the aforementioned embodiments. For example, in one embodiment, a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in crystalline solid state form is characterised by an X-ray powder diffraction (XRPD) pattern substantially as shown in FIG. 1 and a $^{13}$C SSNMR spectrum substantially as shown in FIG. 2. In another illustrative embodiment, a benzene sulphonic acid salt of 2-[(4S)-6-(4-chlorophenyl)-1-methyl-8-(methyloxy)-4H-[1, 2,4]triazolo[4,3-a][1,4]benzodiazepin-4-yl]-N-ethylacetamide in crystalline solid state form is characterised by an X-ray powder diffraction (XRPD) pattern comprising diffraction angles, expressed in degrees 2θ, at about 5.5, 10.0, 18.7, 20.4, and 23.1° (±0.1°) and a $^{13}$C SSNMR spectrum substantially as shown in FIG. 2.

The invention further provides for a process for preparing a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide comprising contacting 2-[(4S)-6-(4-chlorophenyl)-1-methyl-8-(methyloxy)-4H-[1, 2,4]triazolo[4,3-a][1,4]benzodiazepin-4-yl]-N-ethylacetamide or a solvate thereof with benzene sulphonic acid.

It has been found that a benzene sulphonic acid salt of 2-[(4S)-6-(4-chlorophenyl)-1-methyl-8-(methyloxy)-4H-[1, 2,4]triazolo[4,3-a][1,4]benzodiazepin-4-yl]-N-ethylacetamide with an improved impurity profile can be obtained by reaction of benzene sulphonic acid with an acetonitrile solvate of 2-[(4S)-6-(4-chlorophenyl)-1-methyl-8-(methyloxy)-4H-[1,2,4]triazolo[4,3-a][1,4]benzodiazepin-4-yl]-N-ethylacetamide benzene. In one embodiment there is provided a process for preparing a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide which comprises contacting an acetonitrile solvate of 2-[(4S)-6-(4-chlorophenyl)-1-methyl-8-(methyloxy)-4H-[1, 2,4]triazolo[4,3-a][1,4]benzodiazepin-4-yl]-N-ethylacetamide with benzene sulphonic acid. Typically the reaction is carried out in a suitable organic solvent such as 2-methyltetrahydrofuran or a mixture of solvents such as acetonitrile and 2-methyltetrahydrofuran.

The intermediate, the acetonitrile solvate of 2-[(4S)-6-(4-chlorophenyl)-1-methyl-8-(methyloxy)-4H-[1,2,4]triazolo [4,3-a][1,4]benzodiazepin-4-yl]-N-ethylacetamide, that is to say the compound of formula (Ia)

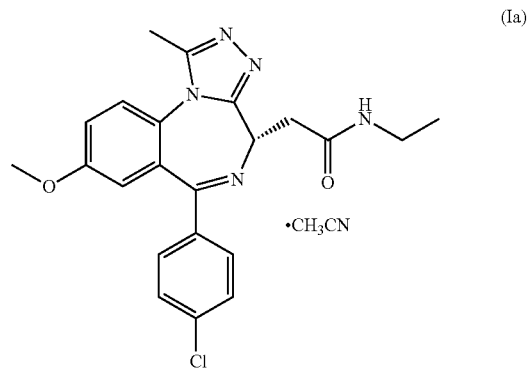 [SMILES: CCNC(=O)C[C@@H]1N=C(c2ccc(Cl)cc2)c2cc(OC)ccc2-n2c(C)nnc21]

(Ia)

forms a yet further aspect of the invention. This intermediate compound can be prepared by procedures described herein.

A benzene sulphonic acid salt of 2-[(4S)-6-(4-chlorophenyl)-1-methyl-8-(methyloxy)-4H-[1,2,4]triazolo[4,3-a][1,4] benzodiazepin-4-yl]-N-ethylacetamide can also be prepared according to procedures outlined herein and by procedures outlined in Scheme 1.

Scheme 1
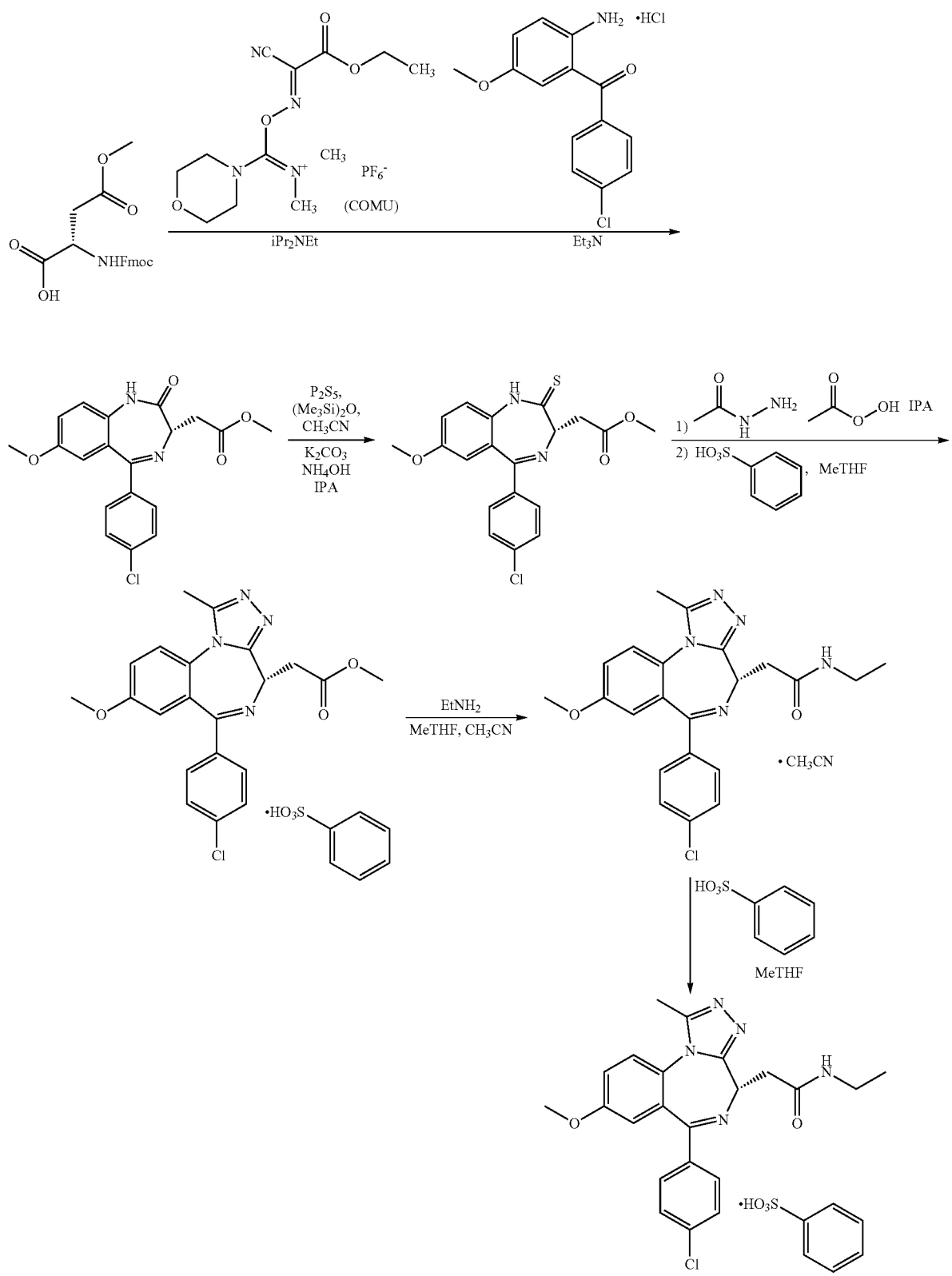
Abbreviations
MeTHF - 2methyltetrahydrofuran
IPA - isopropylalcohol
Fmoc - 9-fluorenylmethoxycarbonyl A benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide is a bromodomain inhibitor, more particularly a BET family bromodomain inhibitor, and thus is believed to have potential utility in the treatment of diseases or conditions for which a bromodomain inhibitor is indicated.

The present invention thus provides a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide for use in therapy.

The present invention also provides a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide for use in the treatment of diseases or conditions for which a bromodomain inhibitor is indicated. In a particular embodiment there is provided a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide for use in the treatment of acute or chronic autoimmune and/or inflammatory conditions. In a further embodiment there is provided a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide for use in the treatment cancer.

The present invention further provides for the use of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in the manufacture of a medicament for the treatment of diseases or conditions for which a bromodomain inhibitor is indicated.

The present invention further provides a method of treating diseases or conditions for which a bromodomain inhibitor is indicated in a subject in need thereof which comprises administering a therapeutically effective amount of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide.

Suitably the subject in need thereof is a mammal, particularly a human.

As used herein, the term "effective amount" means that amount of a drug or pharmaceutical agent that will elicit the biological or medical response of a tissue, system, or subject (e.g. a human) that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Bromodomain inhibitors may be useful in the treatment of a wide variety of acute or chronic autoimmune and/or inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolemia, atherosclerosis, Alzheimer's disease, depression, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, Addison's disease, hypophysitis, thyroiditis, type I diabetes, type II diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement and acute rejection of transplanted organs.

In one embodiment the acute or chronic autoimmune and/or inflammatory condition is a disorder of lipid metabolism via the regulation of APO-A1 such as hypercholesterolemia, atherosclerosis and Alzheimer's disease.

In another embodiment the acute or chronic autoimmune and/or inflammatory condition is a respiratory disorder such as asthma or chronic obstructive airways disease.

In another embodiment the acute or chronic autoimmune and/or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease and Ulcerative colitis). In a particular embodiment the acute or chronic autoimmune and/or inflammatory condition is rheumatoid arthritis, in particular refractory (treatment resistant) rheumatoid arthritis.

In another embodiment the acute or chronic autoimmune and/or inflammatory condition is multiple sclerosis.

In a further embodiment the acute or chronic autoimmune and/or inflammatory condition is Type I diabetes.

Bromodomain inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

In one embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

In one embodiment the disease or condition which involves an inflammatory response to an infection with bacteria, a virus, fungi, a parasite or their toxins is acute sepsis.

Bromodomain inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of cardiovascular diseases such as coronary artery diseases (for example, angina and myocardial infarction), cerebro-vascular ischaemia (stroke), heart failure, pulmonary arterial hypertension (PAH), hypertensive heart disease, rheumatic heart disease, cardiomyopathy, atrial fibrillation, congenital heart disease, endocarditis, aortic aneurysms and peripheral artery disease.

In one embodiment the disease or condition for which a bromodomain inhibitor is indicated is pulmonary arterial hypertension (PAH).

Bromodomain inhibitors may be useful in the treatment of fibrotic conditions such as idiopathic pulmonary fibrosis, renal fibrosis, post-operative stricture, keloid scar formation, scleroderma (including morphea) and cardiac fibrosis.

In one embodiment the disease or condition for which a bromodomain inhibitor is indicated is scleroderma (systemic sclerosis).

Bromodomain inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxvirus infections such as cowpox and smallpox and African swine fever virus. In one embodiment the viral infection is a HPV infection of skin or cervical epithelia. In another embodiment the viral infection is a latent HIV infection.

Bromodomain inhibitors may be useful in the treatment of a wide variety of bone disorders such as osteoporosis and osteopenia.

Bromodomain inhibitors may be useful in the treatment of cancer, including hematological (such as leukaemia, lymphoma and multiple myeloma), epithelial including lung, breast and colon carcinomas, midline carcinomas, mesenchymal, hepatic, renal and neurological tumours. Bromodomain inhibitors may be further useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, castration-resistant prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), NUT-midline carcinoma and testicular cancer.

In one embodiment the cancer is a leukaemia, for example a leukaemia selected from acute monocytic leukemia, acute myelogenous leukemia, chronic myelogenous leukemia, chronic lymphocytic leukemia and mixed lineage leukemia (MLL). In a particular embodiment the cancer is acute myelogenous leukemia (AML). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is breast cancer. In another embodiment the cancer is colorectal cancer.

The term "diseases or conditions for which a bromodomain inhibitor is indicated", is intended to include each of or all of the above diseases or conditions.

While it is possible that for use in therapy, a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide may be administered as the raw chemical, it is common to present the active ingredient as a pharmaceutical composition with one or more pharmaceutically acceptable excipient(s). The pharmaceutical composition can be used in the treatment of any of the conditions described herein.

The present invention therefore provides in a further aspect a pharmaceutical composition comprising a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide and one or more pharmaceutically acceptable excipient(s). The excipient(s) must be acceptable in the sense of being compatible with the other ingredients of the composition and not deleterious to the recipient thereof.

In one embodiment, this invention relates to a pharmaceutical composition comprising a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in solid state crystalline form, in particular a crystalline solid state form as specifically described herein. In another embodiment, this invention relates to a pharmaceutical composition comprising a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide wherein at least 10% by weight, or at least 20% by weight, or at least 30% by weight, or at least 40% by weight, or at least 50% by weight, or at least 60% by weight, or at least 70% by weight, or at least 80% by weight, or at least 90% by weight of the benzene sulphonic acid salt is present as the crystalline solid state form as described herein. In another embodiment, this invention relates to a pharmaceutical composition comprising a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide wherein at least 95% by weight, or at least 96% by weight, or at least 97% by weight, or at least 98% by weight, or at least 99% by weight, or at least 99.5% by weight, or at least 99.8% by weight, or at least 99.9% by weight of the benzene sulphonic acid salt is present as the crystalline solid state form as specifically described herein.

In another embodiment, this invention relates to a pharmaceutical composition comprising a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N- ethylacetamide wherein not more than 90% by weight of the benzene sulphonic acid salt is amorphous. In another embodiment, this invention relates to a pharmaceutical composition comprising a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of the benzene sulphonic acid salt is amorphous. In another embodiment, this invention relates to a pharmaceutical composition comprising a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of the benzene sulphonic acid salt is amorphous.

In another embodiment, this invention relates to a pharmaceutical composition comprising a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide wherein not more than 90% by weight of the benzene sulphonic acid salt is present in a form other than the crystalline solid state form as specifically described herein. In another embodiment, this invention relates to a pharmaceutical composition comprising a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of the benzene sulphonic acid salt is present in a crystalline solid state form other than the crystalline solid state form as specifically described herein. In another embodiment, this invention relates to a pharmaceutical composition comprising a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of the benzene sulphonic acid salt is present in a crystalline solid state form other than the crystalline solid state form as specifically described herein.

Suitable compositions may be prepared by any method known in the art of pharmacy, for example by bringing into association the active ingredient with the excipient(s). Suitable methods for formulating a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide include those described herein, methods described in patent application WO2011/054553 and/or the methods that are familiar to those skilled in the art, which are described in Remington: The Science and Practice of Pharmacy, 21$^{st}$ Edition 2006. In accordance with another aspect of the invention there is also provided a process for the preparation of a pharmaceutical composition including admixing a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide with one or more pharmaceutically acceptable excipient(s).

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route.

In one embodiment the pharmaceutical composition is adapted for parenteral administration, particularly intravenous administration.

In one embodiment the pharmaceutical composition is adapted for topical administration.

In a particular embodiment the pharmaceutical composition is adapted for oral administration.

Whilst a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide did not decompose in standard stability studies it has been found that disproportionation may occur when formulated into a tablet dosage form with certain commonly used pharmaceutical excipients (e.g. a disintegrant such as croscarmellose sodium).

The present invention therefore provides a pharmaceutical composition in the form of a tablet comprising a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide and a pharmaceutically acceptable excipient that inhibits disproportionation. In one embodiment the pharmaceutical excipient that inhibits dispropotionation is the disintegrant crospovidone.

It will be appreciated that the pharmaceutical formulation of the present application may comprise further pharmaceutical excipients such as diluents, lubricants, fillers, bulking agent and the like.

In a further embodiment there is provided a pharmaceutical composition in the form of a tablet comprising:
a) a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide;
b) crospovidone;
c) one or more filler or bulking agent(s);
d) one or more diluents(s); and
e) one or more lubricant(s);

In one embodiment the pharmaceutical composition in the form of a tablet is film coated.

A benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide is typically present in a pharmaceutical composition in the form of a tablet amount according to the invention in an amount 0.1-50% w/w, more typically 1-20% w/w.

The disintegrant cropovidone is typically present in the formulation in an amount 1-10%, particularly 2-6% w/w.

Potential fillers or bulking agents for use in the pharmaceutical composition if the invention are familiar to a person skilled in the art and as described in Rowe et al (ed) (Handbook of Pharmaceutical Excipients, 7 Edition, London: Pharmaceutical Press 2012) the contents of which are incorporated by reference. In one embodiment the filler is a cellulose derivative such as microcrystalline cellulose (such as Avicel PH112). Typically the filler or bulking agent is present in an amount 10-90% w/w of the formulation, more typically 25-75% w/w, even more particularly 35-65% w/w or 35-50% w/w.

Potential diluents for use in the pharmaceutical composition of the invention are familiar to a person skilled in the art and as described in Rowe et al (ed) (Handbook of Pharmaceutical Excipients, 7 Edition, London: Pharmaceutical Press 2012) the contents of which are incorporated by reference. Typically the diluent is present in an amount 10-90% w/w of the formulation, more typically 25-75% w/w, even more particularly 35-65% w/w or 35-50% w/w. In one embodiment the diluent is mannitol.

Potential lubricants for use in the pharmaceutical composition of the invention are familiar to a person skilled in the art and as described in Rowe et al (ed) (Handbook of Pharmaceutical Excipients, 7 Edition, London: Pharmaceutical Press 2012) the contents of which are incorporated by reference. Typically the lubricant is present in an amount 0.1-5% w/w of the formulation, more typically 0.5-2.5% w/w. In one embodiment the lubricant is magnesium stearate. In another embodiment the lubricant is sodium stearyl fumerate.

Moreover, when desired or necessary, suitable buffering agents, binders, glidants, sweetening agents, flavours, and colouring agents can also be incorporated into the mixture.

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

A therapeutically effective amount of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide, will depend upon a number of factors including, for example, the age and weight of the subject, the precise condition requiring treatment and its severity, the nature of the formulation, and the route of administration, and will ultimately be at the discretion of the attendant physician. In the pharmaceutical composition, each dosage unit for oral or parenteral administration preferably contains from 0.01 to 3000 mg, more preferably 0.5 to 1000 mg, of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide, calculated as the free base. Each dosage unit for nasal or inhaled administration preferably contains from 0.001 to 50 mg, more preferably 0.01 to 5 mg, of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide, calculated as the free base.

A benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide, can be administered in a daily dose (for an adult patient) of, for example, an oral or parenteral dose of 0.01 mg to 3000 mg per day, 0.5 to 1000 mg per day or 100 mg to 2500 mg per day, or a nasal or inhaled dose of 0.001 to 50 mg per day or 0.01 to 5 mg per day, of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide. This amount may be given in a single dose per day or more usually in a number (such as two, three, four, five or six) of sub-doses per day such that the total daily dose is the same.

A benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide may be employed alone or in combination with other therapeutic agents. Combination therapies according to the present invention comprise the administration of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide, and at least one other therapeutically active agent. A benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide, and the other therapeutically active agent(s) may be administered together in a single pharmaceutical composition or separately and, when administered separately this may occur simultaneously or sequentially in any order. The amounts of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide, and the other therapeutically active agent(s) and the relative timings of administration will be selected in order to achieve the desired combined therapeutic effect.

Thus in a further aspect, there is provided a combination pharmaceutical product comprising a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide, together with one or more other therapeutically active agents.

Thus in one embodiment, a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide and pharmaceutical compositions comprising such a compound according to the invention may be used in combination with or include one or more other therapeutic agents, for example selected from antibiotics, anti-virals, glucocorticosteroids, muscarinic antagonists beta-2 agonists and Vitamin D3 analogues. In a further embodiment a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide may be used in combination with a further therapeutic agent which is suitable for the treatment of cancer. Examples of such further therapeutic agents are described in Cancer Principles and Practice of Oncology by V. T. Devita and S. Hellman (editors), 6$^{th}$ edition (2001), Lippincott Williams & Wilkins Publishers. A person of ordinary skill in the art would be able to discern which combinations of agents would be useful based on the particular characteristics of the drugs and the cancer involved. Further therapeutic agents to be used in combination with the compound which is a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide include, but are not limited to, anti-microtubule agents (such as diterpenoids and vinca alkaloids); platinum coordination complexes; alkylating agents (such as nitrogen mustards, oxazaphosphorines, alkylsulphonates, nitrosoureas, and triazenes); antibiotic agents (such as anthracyclins, actinomycins and bleomycins); topoisomerase II inhibitors (such as epipodophyllotoxins); antimetabolites (such as purine and pyrimidine analogues and anti-folate compounds); topoisomerase I inhibitors (such as camptothecins; hormones and hormonal analogues); signal transduction pathway inhibitors (such as tyropsine receptor inhibitors); non-receptor tyrosine kinase angiogenesis inhibitors; immunotherapeutic agents; proapoptotic agents; epigenetic or transcriptional modulators (such as histone deacetylase inhibitors), cell cycle signaling inhibitors and inhibitors of hormone nuclear receptors.

It will be appreciated that when a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide, is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable excipient represent a further aspect of the invention.

The following Examples serve to illustrate the invention and are not to be considered as limiting the scope of the invention in any way.

Example 1

Preparation of an acetonitrile solvate of 2-[(4S)-6-(4-chlorophenyl)-1-methyl-8-(methyloxy)-4H-[1,2,4]triazolo[4,3-a][1,4]benzodiazepin-4-yl]-N-ethylacetamide Amorphous 2-[(4S)-6-(4-chlorophenyl)-1-methyl-8-(methyloxy)-4H-[1,2,4]triazolo[4,3-a][1,4]benzodiazepin-4-yl]-N-ethylacetamide (prepared for instance as described in WO2011/054553, 1 wt) was dissolved in acetonitrile (20 vol) upon heating (up to reflux). The solution was then distilled to 10 vol keeping the temp 50° C.-60° C. by adjusting the vacuum. Nucleation occurred during the final stage of the distillation. The slurry was then held at 60° C. before being cooled to 20° C. and filtered. The cake was then washed with acetonitrile (2 vol). The cake was dried under vacuum with a nitrogen bleed at approximately 60° C. to provide the titled product.

$^1$H-NMR (500 MHz, DMSO-$d_6$, referenced to TMS=0.00 ppm, T=25 C) δ ppm 8.22 (1H, t, J=5 Hz), 7.79 (1H, d, J=9 Hz), 7.53 (2H, d, J=9 Hz), 7.49 (2H, d, J=9 Hz), 7.38 (1H, dd, J=3 Hz, 9 Hz), 6.87 (1H, d, J=3 Hz), 4.49 (1H, m), 3.79 (3H, s), 3.25 (1H, m), 3.20-3.06 (3H, several m), 2.54 (3H, s), 2.08 (3H, s), 1.07 (3H, t, J=7 Hz).

Example 2

Preparation of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in crystalline solid state form Preparation 1

The acetonitrile solvate of 2-[(4S)-6-(4-chlorophenyl)-1-methyl-8-(methyloxy)-4H-[1,2,4]triazolo[4,3-a][1,4]benzodiazepin-4-yl]-N-ethylacetamide (for a preparation see Example 1, 2.58 g) was slurried in acetonitrile (7 mL) and 2-methyltetrahydrofuran (7 mL). Benzenesulfonic acid (1.17 g) was dissolved in acetonitrile (7 mL). The resulting solution was charged to the slurry of 2-[(4S)-6-(4-chlorophenyl)-1-methyl-8-(methyloxy)-4H-[1,2,4]triazolo[4,3-a][1,4]benzodiazepin-4-yl]-N-ethylacetamide acetonitrile solvate in acetonitrile and 2-methyltetrahydrofuran. An additional rinse of acetonitrile (1.4 mL) and 2-methyltetrahydrufran (0.7 mL) was added to the slurry. The slurry was then warmed to 60° C. to dissolve. 2-methyltetrahydrofuran (50 mL) was then added over 30 minutes. Crystals formed during this addition. The resulting suspension was then cooled to 5° C. at a controlled, linear rate of 0.5° C./minute. The slurry was aged for 1 hour. The crystalline product was then isolated by filtration and rinsed with a 5 to 1 mixture of 2-methyltetrahydrofuran and acetonitrile (15 mL). The product was then dried in a vacuum oven at 55° C. overnight.

Preparation 2

The acetonitrile solvate of 2-[(4S)-6-(4-chlorophenyl)-1-methyl-8-(methyloxy)-4H-[1,2,4]triazolo[4,3-a][1,4]benzodiazepin-4-yl]-N-ethylacetamide (prepared for example in a process such as Example 1 above, 1 wt) was dissolved in 9 vol 2-methyltetrahydrofuran at 65° C. Once cooled to 20° C. the solution was filtered into the crystallization vessel. The dissolution vessel and inline filter were rinsed with 1 vol 2-methyltetrahydrofuran. The solution was then heated to 45° C.

1.05 eq of benzene sulphonic acid was dissolved in 1 volume of filtered acetonitrile. 10% of this solution was added to a reactor to which 0.05 wt % of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide micronized seed (prepared for example as in Preparation 1 above) slurry was charged. The remaining benzene sulphonic acid solution was charged at a steady rate over 2 hours, maintaining the reactor at 45° C.

The slurry was cooled to 0° C. at no greater than 0.2° C./minute. The slurry was filtered. The crystallizer was charged with the first wash, 3 vol of filtered 2-methyltetrahydrofuran, which was cooled to <10° C. while stirring in the crystallizer, before being used to wash the cake. The crystallizer was charged with the second wash, 3 vol of filtered 2-methyltetrahydrofuran, which was cooled to <10° C. while stirring in the crystallizer, before being used to wash the cake. The crystallizer was charged with the third wash, 4 vol of filtered 2-MeTHF, which was cooled to <10° C. while stirring in the crystallizer, before being used to wash the cake. The cake was blown-down until the solvent being removed was reduced to a trickle. The title compound was then dried in a vacuum oven at 50° C. until the loss on drying (LOD) indicates <0.2% wt. loss (LOD method: 10 min at 120° C.). The product was then delumped using a comil.

Example 3

Characterisation of a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in crystalline solid state form

XRPD

The X-ray powder diffraction (XRPD) data were acquired on a PANalytical X'Pert Pro powder diffractometer, model PW3050/60, using an X'Celerator detector. The acquisition conditions were: radiation: Cu Kα, generator tension: 45 kV, generator current: 40 mA, step size: 0.017°2θ, time per step:

500 seconds, divergence slit type: fixed, divergence slit size: 0.4354°, measurement temperature: 20-25° C., goniometer radius: 240 mm. The sample was prepared by packing sample in a 0.9 mm capillary. Peak positions were obtained using PANalytical X'Pert Highscore Plus software. The margin of error is approximately ±0.1°2θ for each of the peak assignments.

The X-ray powder diffraction (XRPD) pattern is shown in FIG. 1 and shows characteristic peaks, expressed in degrees 2θ, at 5.5, 7.4, 9.1, 10.0, 10.4, 13.3, 13.6, 14.9, 18.7, 20.4, 20.9, 22.8 and 23.1° (±0.1°).

$^{13}$C Solid State NMR (SSNMR)

A $^{13}$C SSNMR spectrum was obtained at 273 K on a spectrometer operating at a frequency of 100.56 MHz for $^{13}$C observation using a cross-polarization pulse sequence with a Bruker 4-mm triple resonance magic-angle spinning probe at a rotor frequency of 8 kHz. The margin of error is ±0.2 ppm for each of the peak assignments.

The $^{13}$C SSNMR spectrum is shown in FIG. 2 and comprises chemical shifts (ppm) at 169.6, 167.5, 165.6, 160.1, 159.4, 157.1, 155.9, 154.3, 152.4, 146.9, 145.8, 140.0, 137.9, 135.9, 133.4, 132.0, 130.6, 129.9, 128.3, 127.1, 125.6, 123.5, 120.6, 119.1, 114.1, 113.7, 58.0, 53.6, 53.1, 40.7, 37.0, 34.9, 15.8, 14.7, and 12.0 (±0.2 ppm).

Example 4

Pharmaceutical compositions comprising a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide suitable for oral administration The compositions as described in Table 1 were prepared. A benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in crystalline solid state form (active), mannitol, microcrystalline cellulose and crospovidone were mixed in a bin blender. Magnesium stearate was later added with further mixing. The resultant blend was compressed in a rotary tablet press. The tablet was coated with an Opaday® coating.

TABLE 1

| | mg/tablet (% w/w) | | | | | |
|---|---|---|---|---|---|---|
| Component | 5 mg | | 25 mg | | 50 mg | |
| Tablet Strength | % w/w | mg | % w/w | mg | % w/w | mg |
| Active | 4.57 | 6.85 | 13.70 | 34.25 | 13.70 | 68.50 |
| Mannitol Pearlitol SD200 | 60.43 | 90.65 | 51.30 | 128.25 | 51.30 | 256.50 |
| Microcrystalline cellulose, PH112 | 30.00 | 45.00 | 30.00 | 75.00 | 30.00 | 150.00 |
| Crospovidone | 4.00 | 6.00 | 4.00 | 10.00 | 4.00 | 20.00 |
| Magnesium stearate | 1.00 | 1.50 | 1.00 | 2.50 | 1.00 | 5.00 |
| Uncoated tablet weight | 100.00 | 150.00 | 100.00 | 250.00 | 100.00 | 500.00 |
| Film Coating | Weight Gain | | | | | |
| | — | 4.5 | — | 7.5 | — | 15 |
| Coated Tablet Weight (mg) | — | 154.5 | — | 257.50 | — | 515.00 |
| Tablet Shape | — | Round | — | Round | — | Oval |

The compositions as described in Table 2 were also prepared comprising a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in crystalline solid state form as the active component. The compositions were formed into a tablet and provided with an Opaday® coating.

TABLE 2

| | mg/tablet (% w/w) | | | | | |
|---|---|---|---|---|---|---|
| Component | 5 mg | | 25 mg | | 50 mg | |
| Tablet Strength | % w/w | mg | % w/w | mg | % w/w | mg |
| Active | 4.57 | 6.85 | 15.22 | 34.25 | 15.22 | 68.50 |
| Mannitol Pearlitol SD200 | 45.22 | 67.825 | 39.89 | 89.75 | 39.89 | 179.50 |
| Microcrystalline cellulose, PH112 | 45.22 | 67.825 | 39.89 | 89.75 | 39.89 | 179.50 |
| Crospovidone | 4.00 | 6.00 | 4.00 | 9.00 | 4.00 | 18.00 |
| Magnesium stearate | 1.00 | 1.50 | 1.00 | 2.25 | 1.00 | 4.50 |
| Uncoated tablet weight | 100 | 150.00 | 100 | 225.00 | 100 | 450.00 |
| Tablet Shape | | Round | | Round | | Oval |

Example 5

Stability studies carried out on a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in crystalline solid state form A batch of benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in crystalline solid state form was packaged in double polyethylene bags, sealed with plastic ties, and placed in HDPE bottles with and without desiccant. Samples were placed on storage at 25° C./60% RH, 30° C./65% RH, 40° C./75% RH, 50° C./AmbH and exposed to photostability conditions (exposed and protected) in accordance with ICH Q1B. Tests for description, content, drug-related impurities content, chiral purity, water and solid state form by XRPD are performed at regular intervals.

The results demonstrate both chemical and physical stability after storage at 12 months at 25° C./60% RH at non-desiccated conditions, 12 months at 30° C./65% RH at desiccated and non-desiccated conditions, 6 months at 40° C./75% RH at desiccated and non-desiccated conditions and 3 months at 50° C./AmbH at desiccated and non-desiccated conditions. No significant changes were observed in description, content, drug-related impurities content and chiral purity. Additionally, no change was observed in the solid state form. Water content increased measurably only at 50° C./AmbH without desiccant (0.15%), at 25° C./60% RH after 12 months without desiccant (0.12%), and at 30° C./65% RH after 12 month with and without desiccant (0.10%). No other change to form or impurity profile was observed. The exposed photostability sample showed a change in colour from "white to almost white solid" at initial to "white and slightly yellow solid" after light stressing. There was only a measurable increase in the levels of impurities (total impurity profile of 0.44%) in the photostability exposed sample.

The invention claimed is:

1. A benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide in crystalline solid state form.

2. The crystalline solid state form according to claim 1 characterised by an X-ray powder diffraction (XRPD) pattern substantially as shown in FIG. 1.

3. The crystalline solid state form according to claim 1 characterised by an X-ray powder diffraction pattern comprising at least three diffraction angles, expressed in degrees 2θ, selected from a group consisting of about 5.5, 7.4, 9.1, 10.0, 10.4, 13.3, 13.6, 14.9, 18.7, 20.4, 20.9, 22.8 and 23.1° (±0.1°).

4. The crystalline solid state form according to claim 1 characterised by a $^{13}$C SSNMR spectrum substantially as shown in FIG. 2.

5. The crystalline solid state form according to claim 1 characterised by a $^{13}$C SSNMR spectrum comprising at least ten peaks, expressed as chemical shifts in ppm, selected from a group consisting of peaks at about 169.6, 167.5, 165.6, 160.1, 159.4, 157.1, 155.9, 154.3, 152.4, 146.9, 145.8, 140.0, 137.9, 135.9, 133.4, 132.0, 130.6, 129.9, 128.3, 127.1, 125.6, 123.5, 120.6, 119.1, 114.1, 113.7, 58.0, 53.6, 53.1, 40.7, 37.0, 34.9, 15.8, 14.7, and 12.0 (±0.2 ppm).

6. A pharmaceutical composition comprising the benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide according to claim 1 and a pharmaceutically acceptable excipient.

7. The pharmaceutical composition according to claim 6 which is adapted for oral administration.

8. The pharmaceutical composition according to claim 7 in the form of a tablet comprising a pharmaceutically acceptable excipient that inhibits disproportionation.

9. The pharmaceutical composition according to claim 8 in which the pharmaceutically acceptable excipient that inhibits disproportionation is crospovidone.

10. A process for preparing a benzene sulphonic acid salt of 2-[(4S)-6-(4-chlorophenyl)-1-methyl-8-(methyloxy)-4H-[1,2,4]triazolo[4,3-a][1,4]benzodiazepin-4-yl]-N-ethylacetamide according to claim 1 comprising contacting 2-[(4S)-6-(4-chlorophenyl)-1-methyl-8-(methyloxy)-4H-[1,2,4]triazolo[4,3-a][1,4]benzodiazepin-4-yl]-N-ethylacetamide or a solvate thereof with benzene sulphonic acid.

11. The process according to claim 10 which comprises contacting an acetonitrile solvate of 2-[(4S)-6-(4-chlorophenyl)-1-methyl-8-(methyloxy)-4H-[1,2,4]triazolo[4,3-a][1,4]benzodiazepin-4-yl]-N-ethylacetamide with benzene sulphonic acid.

* * * * *